(12) United States Patent
Oda

(10) Patent No.: US 9,164,028 B2
(45) Date of Patent: Oct. 20, 2015

(54) SPECTROMETRIC MEASUREMENT DEVICE AND PROGRAM

(75) Inventor: Ryutaro Oda, Kyoto (JP)

(73) Assignee: SHIMADZU CORPORATION, Kyoto-shi (JP)

(*) Notice: Subject to any disclaimer, the term of this patent is extended or adjusted under 35 U.S.C. 154(b) by 666 days.

(21) Appl. No.: 13/445,210

(22) Filed: Apr. 12, 2012

(65) Prior Publication Data

US 2012/0262711 A1 Oct. 18, 2012

(30) Foreign Application Priority Data

Apr. 14, 2011 (JP) ................. 2011-090155

(51) Int. Cl.
| | |
|---|---|
| G01J 3/42 | (2006.01) |
| G01N 21/31 | (2006.01) |
| G01N 21/64 | (2006.01) |
| G01J 3/06 | (2006.01) |
| G01J 3/18 | (2006.01) |
| G01J 3/44 | (2006.01) |
| G01J 3/02 | (2006.01) |
| G01N 21/27 | (2006.01) |
| G01J 3/28 | (2006.01) |

(52) U.S. Cl.
CPC ............... *G01N 21/31* (2013.01); *G01J 3/024* (2013.01); *G01J 3/027* (2013.01); *G01J 3/0208* (2013.01); *G01J 3/0216* (2013.01); *G01J 3/06* (2013.01); *G01J 3/18* (2013.01); *G01J 3/4406* (2013.01); *G01N 21/274* (2013.01); *G01N 21/64* (2013.01); *G01J 2003/2869* (2013.01); *G01N 2021/6417* (2013.01)

(58) Field of Classification Search
CPC ... G01N 21/274; G01J 3/42; G01J 2003/2869
See application file for complete search history.

(56) References Cited

U.S. PATENT DOCUMENTS

| | | | | |
|---|---|---|---|---|
| 4,176,957 A | * | 12/1979 | Maeda et al. ................. | 356/319 |
| 4,893,259 A | * | 1/1990 | Grosser et al. ................ | 356/317 |
| 5,933,792 A | * | 8/1999 | Andersen et al. .............. | 702/32 |
| 6,629,041 B1 | * | 9/2003 | Marbach ........................ | 702/30 |
| 2006/0152726 A1 | * | 7/2006 | Larsen et al. ................ | 356/416 |

FOREIGN PATENT DOCUMENTS

| | | |
|---|---|---|
| CN | 101201322 A | 6/2008 |
| JP | 2001-83093 A | 3/2001 |
| JP | 2002-296185 A | 10/2002 |

OTHER PUBLICATIONS

Office Action dated Jan. 30, 2014, issued in Chinese Patent Application No. 201210109429.5 with Partial English Translation (14 pages).

* cited by examiner

*Primary Examiner* — Kara E Geisel
(74) *Attorney, Agent, or Firm* — Westerman, Hattori, Daniels & Adrian, LLP

(57) ABSTRACT

A spectrometric measurement device capable of determining an optimal wavelength for detecting an objective component is provided. One mode of the present invention is a fluorescence measurement device for casting an excitation light of a predetermined wavelength into or onto a sample and detecting a predetermined wavelength of light contained in the fluorescence generated from the sample irradiated with the excitation light.

6 Claims, 7 Drawing Sheets ic measurement device to provide a spectrometric measurement device

SPECTROMETRIC MEASUREMENT DEVICE AND PROGRAM

TECHNICAL FIELD

The present invention relates to a spectrometric measurement device and a program for such a device.

BACKGROUND ART

Spectrometric measurement devices, such as fluorescence measurement devices or absorbance determination devices, are a type of system for detecting or determining an objective component in a sample by a spectroscopic method.

A fluorescence measurement device normally has an excitation spectroscopic system for separating a predetermined wavelength of light from the light generated by a light source and irradiating a sample with the separated light as excitation light, a fluorescent spectroscopic system for separating a predetermined wavelength of light from the light emitted from the sample upon irradiation with the excitation light, and a photodetector for detecting the light separated by the fluorescent spectroscopic system and producing a signal corresponding to the amount of the detected light (for example, refer to Patent Document 1).

The wavelength of the excitation light necessary for bringing a substance from the ground state to an excited state and the wavelength of the fluorescence which the substance emits when returning from the excited state to the ground state depend on the kind of substance. Accordingly, in a measurement using a fluorescence measurement device, the excitation wavelength to be used in the measurement and the fluorescence wavelength to be detected with the photodetector must be appropriately set for the component to be detected (i.e. objective component). In a measurement using a conventional fluorescence measurement device, the optimal excitation and fluorescence wavelengths for detecting the objective component are previously determined as follows:

(1) With only a solvent present in a sample cell, a spectrum showing the fluorescence intensity at each fluorescence wavelength is obtained by varying the fluorescence wavelength while maintaining the excitation wavelength at a fixed value. (This spectrum is hereinafter called the "fluorescence-side spectrum.")

(2) With an objective component and the solvent present in the sample cell, a fluorescence-side spectrum is similarly obtained.

(3) The fluorescence-side spectrum of the objective component is obtained by subtracting the spectrum obtained in Step (1) from the spectrum obtained in Step (2), and the wavelength at which the fluorescence intensity is maximized in the obtained spectrum is selected as the optimal fluorescence wavelength.

(4) With only the solvent present in the sample cell, a fluorescent spectrum showing the fluorescence intensity at each excitation wavelength is obtained by varying the excitation wavelength while maintaining the fluorescence wavelength at a fixed value. (This spectrum is hereinafter called the "excitation-side spectrum.")

(5) With the objective component and the solvent present in the sample cell, an excitation-side spectrum is similarly obtained.

(6) The excitation-side spectrum of the objective component is obtained by subtracting the spectrum obtained in Step (4) from the spectrum obtained in Step (5), and the wavelength at which the fluorescence intensity is maximized in the obtained spectrum is selected as the optimal excitation wavelength.

It should be noted that the measurements of the fluorescence-side spectrum and the excitation-side spectrum may be performed in reverse order.

By the previously described method, the excitation wavelength and the fluorescence wavelength at which the highest fluorescence intensity is obtained can be respectively selected as the optimal excitation wavelength and the optimal fluorescence wavelength.

On the other hand, an absorbance determination device normally has an irradiation optical system for separating a predetermined wavelength of light from the light generated by a light source and irradiating a sample with the separated light as the irradiation light and a photodetector for detecting the light that has passed through the sample (transmission light) and producing a signal corresponding to the amount of the detected light.

The wavelength of the light absorbed by a substance depends on the kind of substance. Accordingly, in a measurement using an absorbance determination device, the wavelength of the irradiation light used in the measurement must be appropriately set for the component to be detected (i.e. objective component). Therefore, in a measurement using a conventional absorbance determination device, it is necessary to obtain information about the absorption wavelength of the objective component beforehand by referring to an appropriate document or the like, or to determine the optimal wavelength for the measurement of the objective component as follows:

(1) With only a solvent present in a sample cell, an absorption spectrum is obtained by varying the wavelength of the irradiation light.

(2) With the objective component and the solvent present in the sample cell, an absorption spectrum is similarly obtained.

(3) The absorption spectrum of the objective component is obtained by subtracting the spectrum obtained in Step (1) from the spectrum obtained in Step (2), and the wavelength at which the absorbance is maximized in the absorption spectrum is selected as the optimal wavelength.

BACKGROUND ART DOCUMENT

Patent Document

Patent Document 1: JP-A 2001-83093

SUMMARY OF THE INVENTION

Problem to be Solved by the Invention

However, when any of the previously described methods for determining the optimal wavelength is applied to a fluorescence measurement device or absorbance determination device used as a detector for a liquid chromatograph, the determined wavelengths may possibly be different from the wavelength at which the highest signal-to-noise (S/N) ratio for the liquid chromatograph analysis (and hence the smallest detection limit) is obtained. This is due to the fact that the previously described method for determining the optimal wavelength does not consider the change in the baseline in the liquid chromatograph system, i.e. the magnitude of noise during the process of supplying the mobile phase.

Accordingly, the problem to be solved by the present invention is to provide a spectrometric measurement device capable of determining, as the optimal wavelength, the wavelength at which the S/N ratio is maximized and the detection limit is minimized.

Means for Solving the Problems

The spectrometric measurement device according to the present invention aimed at solving the aforementioned problem is a spectrometric measurement device for casting an irradiation light into or onto a sample and measuring light obtained from the sample due to an interaction between the irradiation light and the sample, including:

a) a data memory for storing first measurement data obtained by using, as the aforementioned sample, a solvent containing no objective component and second measurement data obtained by using, as the aforementioned sample, the solvent containing an objective component, each of the first and second measurement data being obtained by varying, over a predetermined wavelength range, the wavelength of the irradiation light or the wavelength of light to be measured or by dispersing the light obtained from the sample and detecting the dispersed light simultaneously at a plurality of wavelengths within a predetermined range; and b) a sensitivity index estimator for calculating a value indicative of the degree of interaction between the objective component and the irradiation light at each wavelength based on the first measurement data and the second measurement data, for calculating an estimate of the amount of noise due to the solvent at each wavelength from the first measurement data, and for calculating an estimate of a sensitivity index at each wavelength from the ratio between the value indicative of the degree of interaction between the objective component and the irradiation light and the estimate of the amount of noise.

The "ratio between the value indicative of the degree of interaction between the objective component and the irradiation light and the estimate of the amount of noise" may be the ratio of "the value indicative of the degree of interaction between the objective component and the irradiation light" to "the amount of noise due to the solvent" or the ratio of "the amount of noise due to the solvent" to "the value indicative of the degree of interaction between the objective component and the irradiation light." The "sensitivity index" at each wavelength is an index representing the sensitivity level of the measurement at the concerned wavelength. For example, an estimate of the S/N ratio obtained by dividing "the value indicative of the degree of interaction between the objective component and the irradiation light" by "the estimate of the amount of noise due to the solvent" may be used as the sensitivity index. In this case, the larger the value of the sensitivity index is, the higher the sensitivity level of the measurement is. Another example of the sensitivity index is a value obtained by multiplying the concentration of the objective component by "the estimate of the amount of noise due to the solvent" divided by "the value indicative of the degree of interaction between the objective component and the irradiation light." The obtained value corresponds to the detection limit of the concentration. In this case, the smaller the value of the sensitivity index is, the higher the sensitivity level of the measurement is.

In a first mode of the device according to the present invention:

the aforementioned interaction is a fluorescent emission by the sample, and the spectrometric measurement device is a fluorescence measurement device including an excitation optical system for irradiating the sample with an excitation light of a predetermined wavelength and a detection optical system for detecting fluorescence emitted from the sample upon irradiation with the excitation light;

the data memory is used for storing first measurement data obtained by using, as the aforementioned sample, a solvent containing no objective component and second measurement data obtained by using, as the aforementioned sample, the solvent containing an objective component, each of the first and second measurement data being obtained by varying the wavelength of the excitation light over a predetermined wavelength range; and the sensitivity index estimator is designed to calculate a value of the fluorescence intensity of the objective component at each excitation wavelength based on the first measurement data and the second measurement data, to calculate an estimate of the amount of noise due to the solvent at each excitation wavelength from the first measurement data, and to calculate an estimate of the sensitivity index at each excitation wavelength from the ratio between the value of the fluorescence intensity of the objective component and the estimate of the amount of noise.

In a second mode of the device according to the present invention:

the aforementioned interaction is a fluorescent emission by the sample, and the spectrometric measurement device is a fluorescence measurement device including an excitation optical system for irradiating the sample with an excitation light of a predetermined wavelength and a detection optical system for detecting fluorescence emitted from the sample upon irradiation with the excitation light;

the data memory is used for storing first measurement data obtained by using, as the aforementioned sample, a solvent containing no objective component and second measurement data obtained by using, as the aforementioned sample, the solvent containing an objective component, each of the first and second measurement data being obtained by varying, over a predetermined wavelength range, the wavelength of the fluorescence detected by the detection optical system, or by dispersing the fluorescence emitted from the sample and simultaneously detecting the dispersed fluorescence at a plurality of wavelengths within a predetermined range; and the sensitivity index estimator is designed to calculate a value of the fluorescence intensity of the objective component at each fluorescence wavelength based on the first measurement data and the second measurement data, to calculate an estimate of the amount of noise due to the solvent at each fluorescence wavelength from the first measurement data, and to calculate an estimate of the sensitivity index at each fluorescence wavelength from the ratio between the value of the fluorescence intensity of the objective component and the estimate of the amount of noise.

In the first or second mode of the present invention, the sensitivity index estimator may determine the value of the fluorescence intensity of the objective component at each wavelength by subtracting a fluorescent spectrum obtained from the first measurement data from a fluorescent spectrum obtained from the second measurement data, and determine the estimate of the amount of noise due to the solvent at each wavelength by calculating the square root of the value of the fluorescence intensity at each wavelength on the fluorescent spectrum obtained from the first measurement data.

In the fluorescence measurement device used as the detector in a liquid chromatograph system, since a very small amount of light is handled, the noise contained in the fluorescent signal is dominated by a shot noise associated with photoelectric conversion. The magnitude of the shot noise is proportional to the square root of the measured value of the fluorescence intensity, and the difference between the fluorescent spectrum obtained from the second measurement data and the fluorescent spectrum obtained from the first measurement data corresponds to the fluorescent spectrum due to only the objective component. Therefore, by the aforementioned sensitivity index estimator, an estimate of the sensitivity index at each excitation wavelength or fluorescence wavelength can be determined. The estimate of the sensitivity index can be displayed on a monitor or the like to let users know the excitation wavelength or fluorescence wavelength at which the sensitivity is maximized.

In one possible form of the device according to the first or second mode of the present invention:

a reference-light detector for detecting the light cast into or onto the sample is provided; and the sensitivity index estimator calculates the value of the fluorescence intensity of the objective component at each wavelength by subtracting a fluorescent spectrum obtained from the first measurement data from a fluorescent spectrum obtained from the second measurement data, calculates an output current $I_m$ of the fluorescent detector and an output current $I_x$ of the reference-light detector at each wavelength from the first measurement data, and calculates an estimate $\Delta F$ of the amount of noise due to the solvent at each wavelength by the following equation:

$$\Delta F = \frac{I_m}{I_x} \sqrt{B_m/I_m + B_x/I_x}, \quad (1)$$

where $B_m$ is the frequency bandwidth used in the fluorescent detector and its signal processing, and $B_x$ is the frequency bandwidth used in the reference-light detector and its signal processing.

In a more preferable form of the present invention, the spectrometric measurement device is provided with the functions of both the first and second modes so as to inform users of information about both the optimal excitation wavelength and the optimal fluorescence wavelength.

In a third mode of the device according to the present invention:

the aforementioned interaction is an absorption by the sample, and the spectrometric measurement device is an absorbance determination device including an irradiation optical system for casting light into or onto a sample and a transmission-light detector for detecting the light that has passed through the sample;

the data memory is used for storing first measurement data obtained by using, as the aforementioned sample, a solvent containing no objective component and second measurement data obtained by using, as the aforementioned sample, the solvent containing an objective component, each of the first and second measurement data being obtained by varying, over a predetermined wavelength range, the wavelength of the light cast into or onto the sample or the wavelength of the light to be detected, or by dispersing the transmission light from the sample and simultaneously detecting the dispersed transmission light at a plurality of wavelengths within a predetermined range; and the sensitivity index estimator is designed to calculate an absorbance of the objective component at each wavelength based on the first measurement data and the second measurement data, to calculate an estimate of the amount of noise due to the solvent at each wavelength from the first measurement data, and to calculate an estimate of the sensitivity index at each wavelength from the ratio between the absorbance value of the objective component and the estimate of the amount of noise.

In the third mode of the present invention, the sensitivity index estimator may calculate an output current $I_s$ of the transmission-light detector at each wavelength from the first measurement data and calculate an estimate $\Delta A$ of the amount of noise due to the solvent by the following equation:

$$\Delta A = \sqrt{1/I_s} \quad (2)$$

In one possible form of the device according to the third mode of the present invention:

a reference-light detector for detecting the light cast into or onto the sample is provided; and the sensitivity index estimator calculates the absorbance of the objective component at each wavelength by subtracting an absorption spectrum obtained from the first measurement data from an absorption spectrum obtained from the second measurement data, calculates an output current $I$ of the transmission-light detector and an output current $I_0$ of the reference-light detector at each wavelength from the first measurement data, and calculates an estimate $\Delta A$ of the amount of noise due to the solvent at each wavelength by the following equation:

$$\Delta A = \sqrt{B/I + B_0/I_0} \quad (3),$$

where B is the frequency bandwidth used in the transmission-light detector and its signal processing, and $B_0$ is the frequency bandwidth used in the reference-light detector and its signal processing.

In a preferable mode of the present invention, the spectrometric measurement device further includes a wavelength-setting system for setting, as a wavelength to be used in a subsequent measurement, the wavelength at which the estimate of the sensitivity index calculated by the sensitivity index estimator equals a value corresponding to the highest sensitivity level. This configuration is effective for reducing the time and labor for setting the measurement conditions.

The present invention also provides a program for enabling a computer to function as the described previously data memory and sensitivity index estimator.

Effect of the Invention

As described thus far, with the spectrometric measurement device and program according to the present invention, it is possible to determine the wavelength at which the S/N ratio is high and the detection limit is low. Therefore, the measurement can be performed at an optimal wavelength for the detection of the objective component.

BEST MODES FOR CARRYING OUT THE INVENTION

Various modes for carrying out the present invention are hereinafter described by means of embodiments.

First Embodiment

Figure 1:
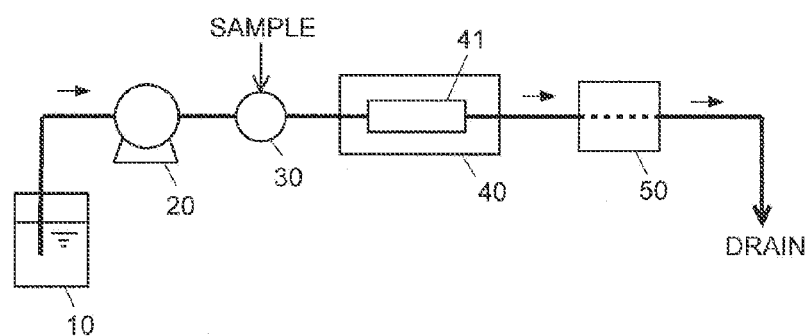
FIG. 1 is a model diagram showing the schematic configuration of a liquid chromatograph system having a fluorescence measurement device according to the first embodiment of the present invention.

FIG. 1 shows the schematic configuration of a liquid chromatograph analyzer system (which is hereinafter called the "LC system") having a fluorescence measurement device according to the present embodiment. This LC system includes a solvent container 10 holding a solvent (i.e. a mobile phase for a chromatographic analysis), a column 41 for separating a sample into components, a pump 20 for feeding the solvent into the column 41, a column oven 40 containing the column 41, and a sample injector 30 for injecting a sample liquid into the solvent fed from the pump 20 into the column 41. In this LC system, the fluorescence measurement device according to the present embodiment is used as a detector 50 for sequentially detecting sample components eluted from the column 41.

Figure 2:
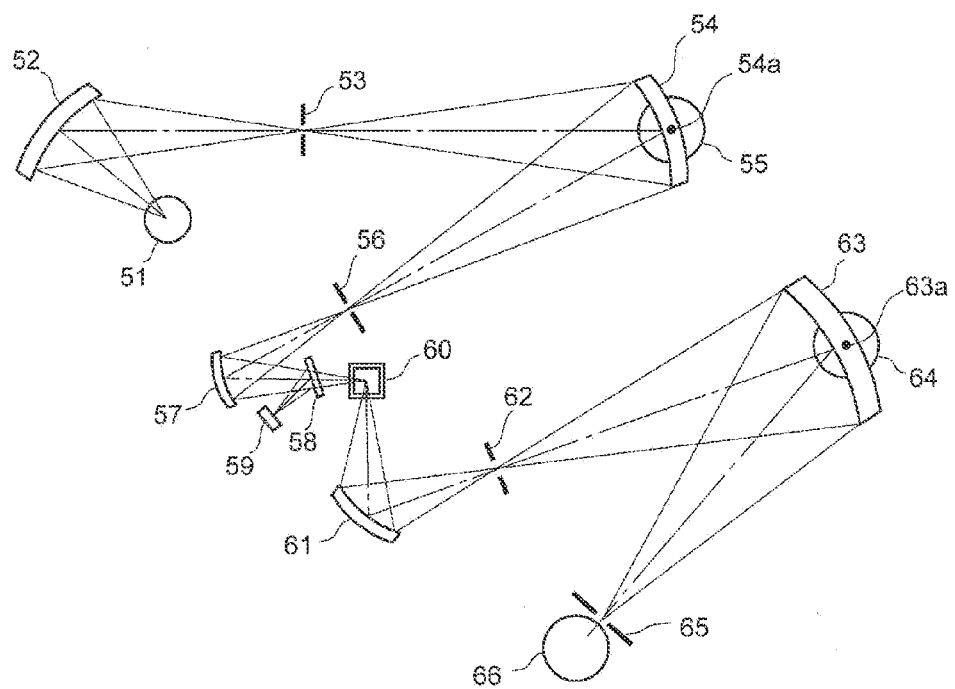
FIG. 2 is a plan view showing the configuration of an optical system of the fluorescence measurement device according to the same embodiment.

FIG. 2 is a diagram showing the schematic configuration of an optical system of the fluorescence measurement device according to the present embodiment. The light generated by a light source 51 (e.g. Xenon lamp) is collected by a collector mirror 52, passes through an excitation-side entrance slit 53 and falls onto an excitation-side diffraction grating 54. The light that has fallen onto the excitation-side diffraction grating 54 is dispersed in the wavelength direction by this grating 54, and a portion of the dispersed light passes through an excitation-side exit slit 56. The portion of light that has passed through the excitation-side exit slit 56 corresponds to the excitation light in the present invention. The excitation-side diffraction grating 54 is provided with an excitation-side grading drive mechanism 55 for rotating this grating 54 about a rotation shaft 54a. The wavelength of the excitation light can be arbitrarily set within a predetermined wavelength range by changing the direction of the grating 54 by this grating drive mechanism 55.

The excitation light that has passed through the excitation-side exit slit 56 is reflected by a collector mirror 57 toward a sample cell 60. A beam splitter 58 is disposed in the optical path between the collector mirror 57 and the sample cell 60 to split the light into two directions. That is to say, a portion of the excitation light passes through the beam splitter 58 and reaches the sample cell 60, while the other portion of the excitation light is reflected by the beam splitter 58 and detected by a reference-light detector (e.g. photodiode) 59. The detection signal produced by the reference-light detector 59 is used to correct the fluctuation of the fluorescent signal due to the fluctuation in the amount of light from the light source.

The excitation light arriving at the sample cell 60 causes the contained sample to emit fluorescence. A portion of this fluorescence is reflected by a collector mirror 61, passes through the fluorescence-side entrance slit 62 and reaches a fluorescence-side diffraction grating 63. The light that has fallen onto the fluorescence-side diffraction grating 63 is dispersed in the wavelength direction by this grating 63, and a portion of the dispersed light passes through a fluorescence-side exit slit 65, to be eventually detected by a fluorescence detector (e.g. photoelectron multiplier) 66. The fluorescence-side diffraction grating 63 is provided with a fluorescence-side grading drive mechanism 64 for rotating this grating 63 about a rotation shaft 63a. The wavelength of the light detected by the fluorescence detector 66 can be arbitrarily set within a predetermined wavelength range by changing the direction of the grating 63 by this grating drive mechanism 64.

Figure 3:
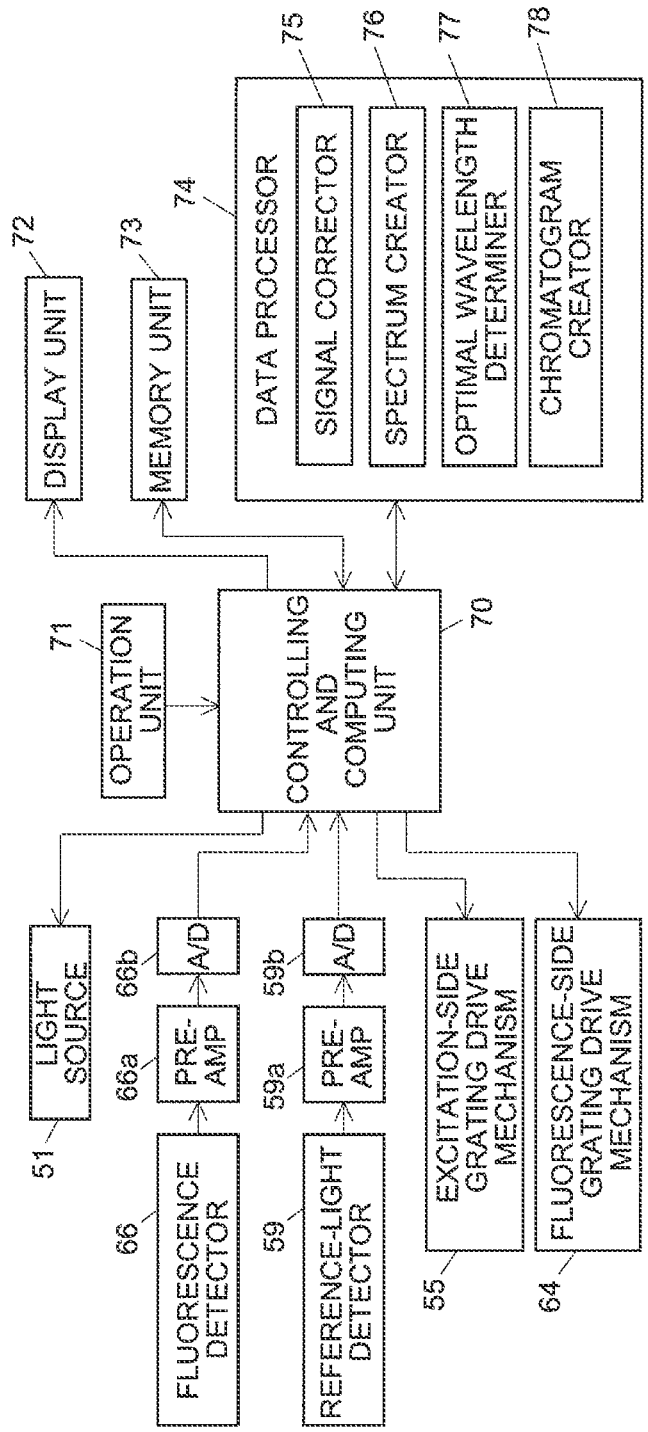
FIG. 3 is a block diagram showing the configuration of a control system of the fluorescence measurement device according to the same embodiment.

FIG. 3 is a block diagram showing the configuration of a control system of the fluorescence measurement device according to the present embodiment. The central component of this control system is a controlling and computing unit 70. Users can enter various commands or setting data into this controlling and computing unit 70 through an operation unit 71. A display unit 72 having a monitor is provided to show measurement results or other information. When a user sets the wavelength for generating an excitation light (excitation wavelength) and/or the wavelength for detecting fluorescence (fluorescence wavelength) and enters a measurement-initiating command into the controlling and computing unit 70, the controlling and computing unit 70 controls the excitation-side grating drive mechanism 55 and the fluorescence-side grating drive mechanism 64 so that the excitation-side diffraction grating 54 and the fluorescence-side diffraction grating 63 will be respectively rotated to the positions corresponding to the set wavelengths, and then energizes the light source 51. It is also possible to scan a predetermined range of excitation wavelength or fluorescence wavelength by controlling the excitation-side grating drive mechanism 55 or fluorescence-side grating drive mechanism 64 so as to rotate the excitation-side diffraction grating 54 or fluorescence-side diffraction grating 63 within a predetermined angular range while the light source 51 is on. (This scan operation will be detailed later.) During the measurement, the output currents of the fluorescence detector 66 and the reference-light detector 59 are respectively converted into voltages in preamplifiers 66a and 59a with a predetermined gain. These voltages are respectively converted into digital data by A/D convertors 66b and 59b. The controlling and computing unit 70 sequentially sends these digital data to a data processor 74.

The data processor 74 includes a signal corrector 75, a spectrum creator 76, an optimal wavelength determiner 77 and a chromatogram creator 78. The signal corrector 75 corrects the output signal from the fluorescence detector 66 by dividing it by the output signal from the reference-light detector 59. The corrected signal is sent to the spectrum creator 76 or chromatogram creator 78 as the fluorescent signal. Based on this fluorescent signal, the chromatogram creator 78 creates a chromatogram showing the temporal change of the fluorescence intensity. On the other hand, the spectrum creator 76, based on the fluorescent signal, creates a fluorescent spectrum showing the fluorescence intensity at each excitation wavelength or fluorescence wavelength. The generated fluorescent spectrum is stored in a memory unit 73. The optimal wavelength determiner 77 performs a predetermined computation based on the spectrum stored in the memory unit 73. (This computation will be detailed later.) It should be noted that the memory unit 73 corresponds to the data memory in the present invention, while the optimal wavelength determiner 77, the signal corrector 75 and the spectrum creator 76 in conjunction with each other function as the sensitivity index estimator in the present invention.

The functions of the data processor 74, the memory unit 73 and other components may be realized by a dedicated computer inside the main body of the fluorescence measurement device, although they are typically realized by a personal computer having a predetermined program installed therein. In the latter case, the personal computer is connected either indirectly to the main body of the fluorescence measurement device via a system controller connected to each of the devices constituting the aforementioned LC system, or directly to the main body of the fluorescence measurement device, and a portion of the functions of the previously described control system is realized by the personal computer.

Figure 4:
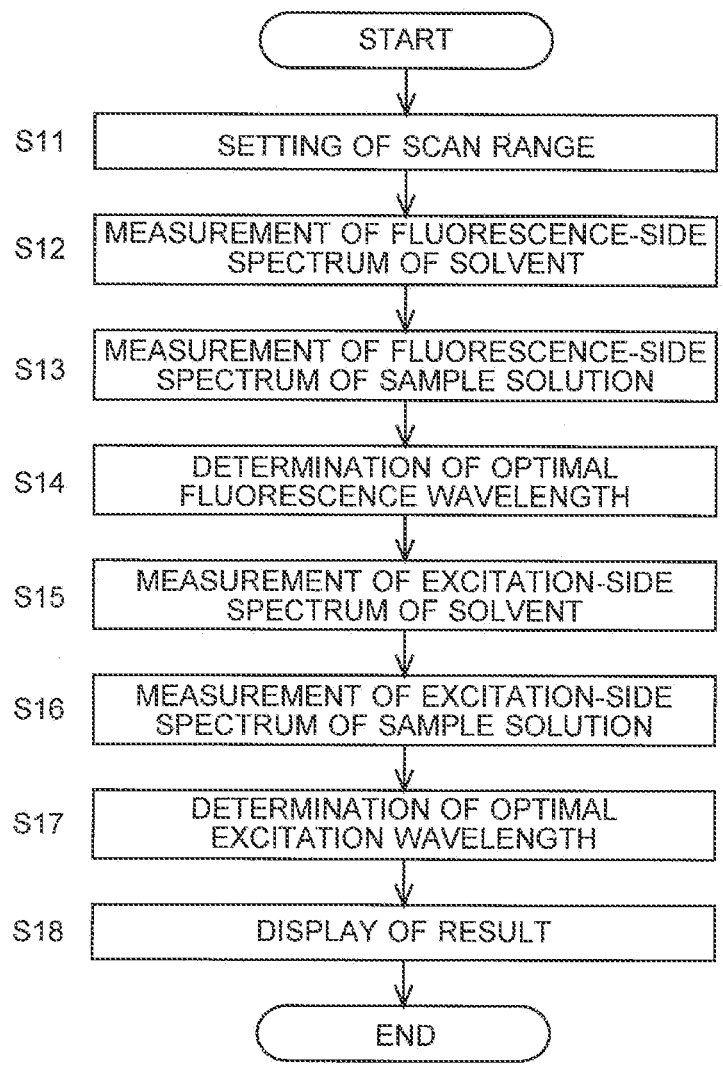
FIG. 4 is a flowchart showing the procedure of determining an optimal wavelength in the fluorescence measurement device according to the same embodiment.

The procedure of determining the optimal fluorescence wavelength and the optimal excitation wavelength by the fluorescence measurement device of the present embodiment is hereinafter described by means of the flowchart of FIG. 4.

(1) Setting of Scan Range (Step S11)

A user performs a predetermined operation on the operation unit 71 to set a range for performing a wavelength scan for each of the excitation and fluorescence wavelengths, the fluorescence wavelength to be used when the wavelength scan is performed on the excitation side, and the excitation wavelength to be used when the wavelength scan is performed on the fluorescence side.

(2) Measurement of Fluorescence-Side Spectrum of Solvent (Step S12)

Subsequently, with only a solvent (mobile phase) contained in the sample cell 60 (contained in a cuvette cell or put in a flow cell), a fluorescent spectrum is obtained by varying the fluorescent wavelength, with the excitation wavelength fixed at the value set in Step S11. Specifically, by using the operation unit 71, the user initially energizes the light source 51 and orders the initiation of the scan of the fluorescence wavelength. In response to this operation, the excitation-side diffraction grating 54 is rotated to a predetermined angle and stopped at that position. Subsequently, the fluorescence-side diffraction grating 63 is rotated over an angular range corresponding to the wavelength range set in Step S11. During this process, the signals produced by the fluorescence detector 66 and the reference-light detector 59 are sent to the data processor 74. In the data processor 74, the signal corrector 75 corrects the output signal of the fluorescence detector 66 by using the output signal of the reference-light detector 59. Based on the obtained fluorescent signal, the spectrum creator 76 creates a spectrum showing the fluorescence intensity at each fluorescence wavelength (this spectrum is hereinafter called the "fluorescence-side spectrum") and stores it in the memory unit 73.

The spectrum creator 76 calculates the output current of the fluorescence detector 66 backward from the output signal of the A/D convertor 66b and the gain of the current-to-voltage conversion by the preamplifier 66a to create a spectrum showing the value of the output current of the fluorescence detector 66 at each wavelength, and stores this spectrum in the memory unit 73. (This spectrum is hereinafter called the "current spectrum of the fluorescence detector.") Similarly, the spectrum creator 76 calculates the output current of the reference-light detector 59 backward from the output signal of the A/D convertor 59b and the gain of the current-to-voltage conversion by the preamplifier 59a to create a spectrum showing the value of the output current of the reference-light detector 59 at each wavelength, and stores this spectrum in the memory unit 73. (This spectrum is hereinafter called the "current spectrum of the reference-light detector.") The set of the fluorescence-side spectrum of the solvent, the current spectrum of the fluorescence detector and the current spectrum of the reference-light detector corresponds to the first measurement data in the device according to the second mode of the present invention.

(3) Measurement of Fluorescence-Side Spectrum of Sample Solution (Step S13)

With the sample cell 60 holding the solvent containing an objective component (this solvent is hereinafter called the "sample solution"), a fluorescence-side spectrum of the sample solution is obtained in the same manner as Step S12 and stored in the memory unit 73. The obtained fluorescence-side spectrum of the sample solution corresponds to the second measurement data in the device according to the second mode of the present invention.

(4) Determination of Optimal Fluorescence Wavelength (Step S14)

After the measurements of the fluorescence-side spectrums are thus completed, the controlling and computing unit 70 reads the spectrums of the solvent obtained in Step S12 and the fluorescence-side spectrum of the sample solution obtained in Step S13 from the memory unit 73 into the data processor 74. In the optimal wavelength determiner 77 of the data processor 74, the fluorescence-side spectrum of the solvent is subtracted from that of the sample solution to obtain the fluorescence-side spectrum of the objective component, and furthermore, an estimate of the amount of noise due to the solvent is computed from the current spectrum of the fluorescence detector and that of the reference-light detector obtained in Step S12.

The amount of noise due to the solvent is estimated as follows: With $I_m$ denoting the output current of the fluorescence detector 66 and $I_x$ denoting the output current of the reference-light detector 59, the shot noise $\Delta I_m$ in the fluorescence detector 66 and the shot noise $\Delta I_x$ in the reference-light detector 59 are respectively expressed by $\Delta I_m = \sqrt{(2qI_m B_m)}$ and $\Delta I_x = \sqrt{(2qI_x B_x)}$, where q is the electron charge, $B_m$ is the frequency bandwidth in the fluorescence detector, and $B_x$ is the frequency bandwidth in the reference-light detector. Normally, $B_m$ and $B_x$ are set to be equal to each other. Furthermore, with $k_m$ denoting the gain of the preamplifier 66a in the fluorescence detector 66 and $k_x$ denoting the gain of the preamplifier 59a in the reference-light detector 59, the fluorescence intensity $F(I_m, I_x)$ can be computed by the following equation:

$$F(I_m, I_x) = \frac{k_m I_m}{k_x I_x} \quad (4)$$

The shot noise $\Delta I_m$ in the fluorescence detector 66 and the shot noise $\Delta I_x$ in the reference-light detector 59 are the standard deviation of the fluctuation of an electric current. The variance $(\Delta F)^2$ of the amount of noise $\Delta F$ is obtained by the following equation:

$$(\Delta F)^2 = \left(\frac{\partial F}{\partial I_m}\Delta I_m\right)^2 + \left(\frac{\partial F}{\partial I_x}\Delta I_x\right)^2 \tag{5}$$

From this equation, an estimate $\Delta F$ of the amount of noise of the solvent can be obtained as follows:

$$\Delta F = \sqrt{\left[\frac{\partial F(I_m, I_x)}{\partial I_m}\right]^2 [\Delta I_m]^2 + \left[\frac{\partial F(I_m, I_x)}{\partial I_x}\right]^2 [\Delta I_x]^2} \tag{6}$$

$$= \sqrt{\left(\frac{k_m}{k_x I_x}\right)^2 2qI_m B_m + \left(\frac{k_m I_m}{k_x I_x^2}\right)^2 2qI_x B_x}$$

$$= \frac{k_m I_m}{k_x I_x}\sqrt{2qB_m/I_m + 2qB_x/I_x}$$

Since the gains $k_x$ and $k_m$ of the preamplifiers as well as the electron charge q are constants, the amount of noise $\Delta F$ can also be expressed as follows:

$$\Delta F \propto \frac{I_m}{I_x}\sqrt{B_m/I_m + B_x/I_x} \tag{7}$$

For the purpose of comparing the levels of S/N ratios at different wavelengths, the amount of noise $\Delta F$ computed by the following equation can be used as an alternative:

$$\Delta F = \frac{I_m}{I_x}\sqrt{B_m/I_m + B_x/I_x} \tag{8}$$

As already noted, the frequency bandwidth $B_m$ in the fluorescence detector and the frequency bandwidth $B_x$ in the reference-light detector are normally set to be equal to each other. In this case, the amount of noise $\Delta F$ calculated by the following equation can be used:

$$\Delta F = \frac{I_m}{I_x}\sqrt{1/I_m + 1/I_x} \tag{9}$$

Then, the optimal wavelength determiner 77 calculates an estimate of the S/N ratio at each wavelength by dividing the value of the fluorescence intensity at each wavelength on the fluorescence-side spectrum of the objective component by the estimate of the amount of noise at the wavelength due to the solvent, and selects, as the optimal fluorescence wavelength, the fluorescence wavelength at which the S/N ratio is maximized.

(5) Measurement of Excitation-Side Spectrum of Solvent (Step S15)

Subsequently, with the sample cell 60 containing only the solvent, a fluorescent spectrum is obtained by varying the excitation wavelength, with the fluorescence wavelength fixed at a predetermined point. The fluorescence wavelength is set at one of the following wavelengths: the fluorescence wavelength set in Step S11, the fluorescence wavelength determined in Step S14 at which the S/N ratio is maximized, and the fluorescence wavelength at which the value of the fluorescence intensity of the florescence-side spectrum of the objective component is maximized. Specifically, the user initially orders the initiation of the scan of the excitation wavelength through the operation unit 71. In response to this operation, the fluorescence-side diffraction grating 63 is rotated to a predetermined angle and stopped at that position. Subsequently, the excitation-side diffraction grating 54 is rotated over an angular range corresponding to the wavelength range set in Step S11. During this process, the signals produced by the fluorescence detector 66 and the reference-light detector 59 are sent to the data processor 74. In the data processor 74, the signal corrector 75 corrects the output signal of the fluorescence detector 66 by using the output signal of the reference-light detector 59. Based on the obtained fluorescent signal, the spectrum creator 76 creates a spectrum showing the fluorescence intensity at each excitation wavelength (this spectrum is hereinafter called the "excitation-side spectrum") and stores it in the memory unit 73.

The spectrum creator 76 calculates the output current of the fluorescence detector 66 backward from the output signal of the A/D convertor 66b and the gain of the current-to-voltage conversion by the preamplifier 66a to create a current spectrum of the fluorescence detector showing the value of the output current of the fluorescence detector 66 at each wavelength, and stores this spectrum in the memory unit 73. Similarly, the spectrum creator 76 calculates the output current of the reference-light detector 59 backward from the output signal of the A/D convertor 59b and the gain of the current-to-voltage conversion by the preamplifier 59a to create a current spectrum of the reference-light detector showing the value of the output current of the reference-light detector 59 at each wavelength, and stores this spectrum in the memory unit 73. The set of the excitation-side spectrum of the solvent, the current spectrum of the fluorescence detector and the current spectrum of the reference-light detector corresponds to the first measurement data in the device according to the first mode of the present invention.

(6) Measurement of Excitation-Side Spectrum of Sample Solution (Step S16)

With the sample cell 60 containing the sample solution, an excitation-side spectrum is obtained in the same manner as Step S15 and stored in the memory unit 73. The obtained excitation-side spectrum of the sample solution corresponds to the second measurement data in the device according to the first mode of the present invention.

(7) Determination of Optimal Excitation Wavelength (Step S17)

By using the obtained excitation-side spectrum, the optimal excitation wavelength is determined by a method similar to Step S14. That is to say, the controlling and computing unit 70 reads the spectrums of the solvent obtained in Step S15 and the excitation-side spectrum data of the sample solution obtained in Step S16 from the memory unit 73 into the data processor 74. In the optimal wavelength determiner 77 of the data processor 74, the excitation-side spectrum of the solvent is subtracted from that of the sample solution to obtain the excitation-side spectrum of the objective component, and furthermore, an estimate of the amount of noise due to the solvent is computed from the current spectrum of the fluorescence detector and that of the reference-light detector obtained in Step S15.

Similar to Step S14, the estimate $\Delta F$ of the amount of noise due to the solvent is computed as follows:

$$\Delta F = \frac{k_m I_m}{k_x I_x}\sqrt{2qB_m/I_m + 2qB_x/I_x} \tag{10}$$

For the purpose of comparing the levels of S/N ratios at different wavelengths, the estimate $\Delta F$ of the amount of noise computed by the following equation can be used:

$$\Delta F = \frac{I_m}{I_x}\sqrt{B_m/I_m + B_x/I_x} \tag{11}$$

When the frequency bandwidth $B_m$ in the fluorescence detector and the frequency bandwidth $B_x$ in the reference-light detector are set to be equal to each other, the estimate $\Delta F$ of the amount of noise calculated by the following equation can be used:

$$\Delta F = \frac{I_m}{I_x}\sqrt{1/I_m + 1/I_x} \quad (12)$$

Then, the optimal wavelength determiner 77 calculates an estimate of the S/N ratio at each wavelength by dividing the value of the fluorescence intensity at each wavelength on the excitation-side spectrum of the objective component by the estimate of the amount of noise at the wavelength due to the solvent, and selects, as the optimal excitation wavelength, the excitation wavelength at which the S/N ratio is maximized.

(8) Display of Result (Step S18)

After the previously described sequential processes have been completed, the controlling and computing unit 70 displays the values of the optimal fluorescence wavelength and the optimal excitation wavelength determined in Steps S14 and S17 on the display unit 72. Instead of the values of the optimal fluorescence wavelength and the optimal excitation wavelength, a graph showing the S/N ratio at each fluorescence wavelength or excitation wavelength may be displayed so that the optimal wavelength can be easily and visually located.

The previously described procedure of determining the optimal fluorescence wavelength and the optimal excitation wavelength was an example for a fluorescence measurement device having a reference-light detector. This example can be modified for the determination of the optimal fluorescence wavelength and the optimal excitation wavelength in a fluorescence measurement device which has no reference-light detector or in which the amount of light received by the fluorescence detector is much smaller than that of the light received by the reference-light detector so that the largest portion of the noise influencing the S/N ratio of the fluorescence measurement device occurs in the fluorescence detector, while the influence of the noise in the reference-light detector is negligible. One such modification is hereinafter illustrated by means of the flowchart of FIG. 4.

(1) Setting of Scan Range (Step S11)

A user performs a predetermined operation on the operation unit 71 to set a range for performing a wavelength scan for each of the excitation and fluorescence wavelengths, the fluorescence wavelength to be used when the wavelength scan is performed on the excitation side, and the excitation wavelength to be used when the wavelength scan is performed on the fluorescence side.

(2) Measurement of Fluorescence-Side Spectrum of Solvent (Step S12)

Subsequently, with only a solvent (mobile phase) contained in the sample cell 60 (contained in a cuvette cell or put in a flow cell), a fluorescent spectrum is obtained by varying the fluorescence wavelength, with the excitation wavelength fixed at the value set in Step S11. Specifically, by using the operation unit 71, the user initially energizes the light source 51 and orders the initiation of the scan of the fluorescence wavelength. In response to this operation, the excitation-side diffraction grating 54 is rotated to a predetermined angle and stopped at that position. Subsequently, the fluorescence-side diffraction grating 63 is rotated over an angular range corresponding to the wavelength range set in Step S11. During this process, the signal produced by the fluorescence detector 66 is sent to the data processor 74. In the data processor 74, based on the obtained fluorescent signal, the spectrum creator 76 creates a spectrum showing the fluorescence intensity at each fluorescence wavelength (this spectrum is hereinafter called the "fluorescence-side spectrum") and stores it in the memory unit 73.

(3) Measurement of Fluorescence-Side Spectrum of Sample Solution (Step S13)

With the sample cell 60 holding the solvent containing an objective component (this solvent is hereinafter called the "sample solution"), a fluorescence-side spectrum is obtained in the same manner as Step S12 and stored in the memory unit 73.

(4) Determination of Optimal Fluorescence Wavelength (Step S14)

After the previously described measurements of the fluorescence-side spectrums are completed, the controlling and computing unit 70 reads the fluorescence-side spectrum of the solvent obtained in Step S12 and the fluorescence-side spectrum of the sample solution obtained in Step S13 from the memory unit 73 into the data processor 74. In the optimal wavelength determiner 77 of the data processor 74, the fluorescence-side spectrum of the solvent is subtracted from that of the sample solution to obtain the fluorescence-side spectrum of the objective component, and furthermore, the value of the fluorescence intensity at each wavelength on the fluorescence-side spectrum of the objective component is divided by the square root of the fluorescence intensity at the corresponding wavelength on the fluorescence-side spectrum of the solvent. Since the noise in the fluorescence detector 66 mostly consists of a shot noise whose magnitude is proportional to the square root of the measured fluorescence intensity, the wavelength at which the value obtained by the aforementioned dividing operation is maximized corresponds to the fluorescence wavelength at which the S/N ratio is maximized (i.e. the optimal fluorescence wavelength.)

(5) Measurement of Excitation-Side Spectrum of Solvent (Step S15)

Subsequently, with the sample cell 60 containing only the solvent, a fluorescent spectrum is obtained by varying the excitation wavelength, with the fluorescence wavelength fixed at a predetermined point. The fluorescence wavelength is set at one of the following wavelengths: the fluorescence wavelength set in Step S11, the fluorescence wavelength determined in Step S14 at which the S/N ratio is maximized, and the fluorescence wavelength at which the value of the fluorescence intensity of the florescence-side spectrum of the objective component is maximized. Specifically, the user initially orders the initiation of the scan of the excitation wavelength through the operation unit 71. In response to this operation, the fluorescence-side diffraction grating 63 is rotated to a predetermined angle and stopped at that position. Subsequently, the excitation-side diffraction grating 54 is rotated over an angular range corresponding to the wavelength range set in Step S11. During this process, the signal produced by the fluorescence detector 66 is sent to the data processor 74. In the data processor 74, based on the obtained fluorescent signal, the spectrum creator 76 creates a spectrum showing the fluorescence intensity at each excitation wavelength (this spectrum is hereinafter called the "excitation-side spectrum") and stores it in the memory unit 73.

(6) Measurement of Excitation-Side Spectrum of Sample Solution (Step S16)

With the sample cell 60 containing the sample solution, an excitation-side spectrum is obtained in the same manner as Step S15 and stored in the memory unit 73.

(7) Determination of Optimal Excitation Wavelength (Step S17)

By using the obtained excitation-side spectrum, the optimal excitation wavelength is determined by a method similar to Step S14. That is to say, the controlling and computing unit 70 reads the excitation-side spectrum of the solvent obtained in Step S15 and the excitation-side spectrum data of the sample solution obtained in Step S16 from the memory unit 73 into the data processor 74. In the optimal wavelength determiner 77 of the data processor 74, the excitation-side spectrum of the solvent is subtracted from that of the sample solution to obtain the excitation-side spectrum of the objective component, and furthermore, the value of the fluorescence intensity at each wavelength on the excitation-side spectrum of the objective component is divided by the square root of the fluorescence intensity at the corresponding wavelength on the excitation-side spectrum of the solvent. The wavelength at which the value obtained by this dividing operation is maximized corresponds to the excitation wavelength at which the S/N ratio is maximized (i.e. the optimal excitation wavelength.)

(8) Display of Result (Step S18)

After the previously described sequential processes have been completed, the controlling and computing unit 70 displays the values of the optimal fluorescence wavelength and the optimal excitation wavelength determined in Steps S14 and S17 on the display unit 72. Instead of the values of the optimal fluorescence wavelength and the optimal excitation wavelength, a graph showing the S/N ratio at each fluorescence wavelength or excitation wavelength may be displayed so that the optimal wavelength can be easily and visually located.

In the previous example, the wavelength at which an estimated S/N ratio obtained by dividing the value of the fluorescence intensity of the objective component by an estimate of the amount of noise due to the solvent is maximized is selected as the optimal wavelength. However, this is not the only possible method. For example, it is possible to use a sample solution containing an objective component at a known concentration, to determine a value corresponding to the detection limit, based on the value obtained by dividing an estimate of the amount of noise due to the solvent by a value of the fluorescence intensity of the objective component at the same wavelength as well as on the concentration of the objective component in the sample solution, and to select, as the optimal wavelength, the wavelength at which the value corresponding to the detection limit is minimized. The order of the measurements for the fluorescence-side spectrum of the solvent, the fluorescence-side spectrum of the sample solution, the excitation-side spectrum of the solvent and the excitation-side spectrum of the sample solution is not limited to the previously described order. For example, the measurements for the fluorescence-side spectrums and the excitation-side spectrums may be performed in reverse order. It is also possible to initially perform the measurements of the solvent for the fluorescence-side spectrum and the excitation-side spectrum, and subsequently the measurements of the sample solution for the fluorescence-side spectrum and the excitation-side spectrum. This method reduces the time and labor for replacing the solvent with the sample solution and vice versa.

A chromatographic analysis by the LC system using the optimal fluorescence wavelength and the optimal excitation wavelength determined in the previously described manner is performed as follows: By using the operation unit 71, the user initially energizes the light source 51 and sets the optimal fluorescence wavelength and the optimal excitation wavelength as the fluorescence wavelength and the excitation wavelength to be used in the measurement. In response to this operation, the excitation-side diffraction grating 54 and the fluorescence-side diffraction grating 63 are respectively rotated to the angles corresponding to the set optimal wavelengths and stopped at that position. Subsequently, when the user orders the initiation of the chromatographic measurement, the device begins the measurement. In this measurement, the solvent and the objective component which are sequentially eluted from the column and pass through the flow cell 60 are analyzed at the optimal excitation wavelength and the optimal fluorescence wavelength, and a chromatogram with the horizontal axis indicating the retention time and the vertical axis indicating the fluorescence intensity is created by the chromatogram creator 78.

As described thus far, with the fluorescence measurement device according to the present invention, it is possible to determine the excitation wavelength and/or the fluorescence wavelength at which the S/N ratio is high and the detection limit is low, so that the measurement can be performed at an optimal wavelength for the detection of the objective component.

In the previous embodiment, when determining the optimal wavelength, the sample to be analyzed (i.e. the solvent or sample solution) is contained in a cuvette cell or put in a flow cell, and the user needs to manually replace the sample and order the initiation of the measurement of the fluorescence-side or excitation-side spectrum. However, it is also possible to configure the fluorescence measurement device according to the present invention so that it automatically performs the measurements of the fluorescence-side spectrum and the excitation-side spectrum at predetermined timings while passing the sample solution through the flow cell. The timing of measuring each of the spectrums may be determined by a scheduling program stored in the memory unit 73 or the like, or it may be determined by detecting the passage of an objective component based on the fluorescent signal produced by the fluorescence detector 66 or other elements.

In the case of performing an automatic measurement by the scheduling program, the user previously creates, through the operation unit 71, a scheduling program in which the spectrum measurement is scheduled to be performed at a first timing corresponding to a predetermined period of time after the injection of the sample and a second timing corresponding to the elution time of the objective component, and stores that program in the memory unit 73. When the solvent eluted from the column 41 begins to pass through the flow cell 60 and the sample is injected into the solvent channel by the sample injector 30, a trigger signal indicating the timing of the sample injection is generated. Upon receiving this trigger signal directly or via a system controller, the controlling and computing unit 70 begins to control each component of the device according to the scheduling program to obtain a fluorescence-side spectrum (or excitation-side spectrum) immediately after the injection of the sample, i.e. at a point in time when only the solvent is present in the flow cell, as well as a fluorescence-side spectrum (or excitation-side spectrum) at a point in time when both the solvent and the objective component are present in the flow cell 60.

In the case of performing an automatic measurement by detecting the passage of an objective component, after the solvent eluted from the column 41 begins to pass through the flow cell 60, the measurement of the fluorescence-side spectrum (or excitation-side spectrum) of the solvent is initially performed immediately after the sample is injected into the solvent channel by the sample injector 30. Subsequently, with the excitation wavelength and the fluorescence wavelength being respectively fixed at the predetermined points, the fluorescent signal is monitored, and when the passage of a sample component is detected from a change in the fluorescence intensity, the measurement of the fluorescence-side spectrum (or excitation-side spectrum) of the solvent containing that component is automatically performed.

In order to more assuredly perform the measurement of the spectrum of the objective component passing through the flow cell 60, it is desirable to temporarily discontinue the flow of the solvent into the flow cell 60 by changing the flow path of the solvent eluted from the column 41 by a channel-switching valve (not shown) or similar device at a timing when the objective component exists in the flow cell 60, and to perform the wavelength scan while the sample component is retained in the flow cell 60.

Second Embodiment

Figure 5:
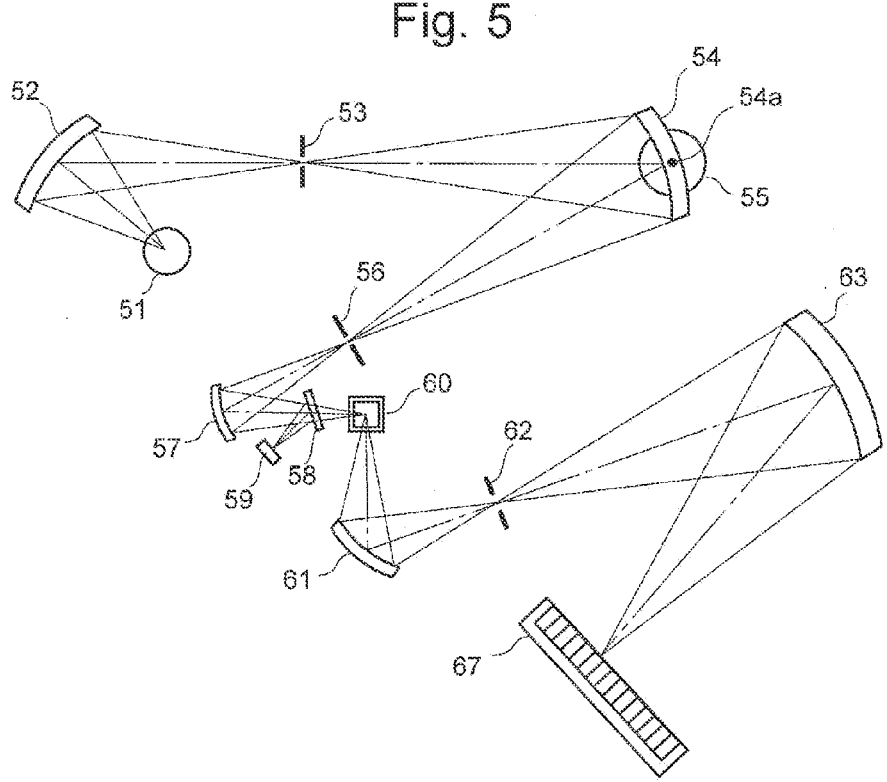
FIG. 5 is a plan view showing the configuration of an optical system of a fluorescence measurement device according to the second embodiment of the present invention.

A fluorescence measurement device according to the second embodiment of the present invention is hereinafter described. FIG. 5 shows one example of the configuration of an optical system of the fluorescence measurement device according to the present embodiment. The same components as shown in FIG. 2 are denoted by the same numerals, and descriptions of such components will be appropriately omitted. The fluorescence measurement device of the present embodiment includes a multi-channel photodetector 67 in place of the fluorescence-side grating drive mechanism 64, the fluorescence-side exit slit 65 and the fluorescence detector 66 for detecting light that has passed through the slit 65. The multi-channel photodetector 67 consists of a plurality of linearly arranged photodetector elements, such as CCDs. In the present embodiment, the fluorescence that has been dispersed into different wavelengths by the fluorescence-side diffraction grating 63 is simultaneously detected by the multi-channel photodetector 67 over a predetermined wavelength range. This optical system eliminates the necessity of varying the fluorescence wavelength and thereby reduces the time required for determining the optimal wavelength. Furthermore, since the three-dimensional data of excitation wavelength, fluorescence wavelength and fluorescence intensity can be obtained by a single scan of the excitation wavelength, it is possible to determine the most suitable excitation wavelength with regard to the combination with each fluorescence wavelength to be used.

Thus far, various modes for carrying out the present invention have been described by means of the embodiments. It should be noted that the present invention is not limited to the previous embodiments but can be appropriately changed within the spirit and scope thereof.

For example, the fluorescence measurement device according to the present invention may include a wavelength-setting system for automatically setting the optimal fluorescence wavelength and/or the optimal excitation wavelength as the fluorescence wavelength and/or the excitation wavelength to be used in the subsequent measurements, in addition to or as an alternative to an informing system for informing a user of the optimal fluorescence wavelength and/or the optimal excitation wavelength. In this case, the excitation wavelength or the fluorescence wavelength at which the estimated S/N ratio is maximized in the calculation by the optimal wavelength determiner 77 is selected as the wavelength to be used in the subsequent measurements and stored in the memory unit 73 by the controlling and computing unit 70. That is to say, in this case, the controlling and computing unit 70 and the memory unit 73 correspond to the wavelength-setting system in the present invention.

The fluorescence measurement device according to the present invention may be provided with the function of creating three-dimensional data composed of the three axes of time, wavelength and fluorescence intensity by repeatedly scanning a range of fluorescence or excitation wavelengths at predetermined intervals of time while passing the solvent and the objective component through the flow cell 60. In this case, the optimal fluorescence wavelength or the optimal excitation wavelength at each point in time after the injection of the sample can be determined by performing the previously described calculation using a spectrum (fluorescent or excitation spectrum) obtained immediately after the injection of the sample as the spectrum of the solvent containing no objective component and a spectrum obtained at a subsequent point in time as the spectrum of the solvent containing the objective component. Therefore, by one injection of the sample, it is possible to determine an optimal wavelength for each of the components contained in the sample. Accordingly, each of the sample components temporally separated by and eluted from the column 41 can be detected at an optimal fluorescence wavelength and/or excitation wavelength by making the LC system perform the analysis while temporally varying the excitation wavelength or the fluorescence wavelength according to a scheduling program in which a previously determined optimal fluorescence wavelength and/or optimal excitation wavelength is set for each point in time after the injection of the sample. Such a scheduling program can be created manually by the user, or automatically by the controlling and computing unit 70, and stored in the memory unit 73.

Furthermore, the fluorescence measurement device according to the present invention may have the function of creating three-dimensional data composed of the three axes of excitation wavelength, fluorescence wavelength and fluorescence intensity by changing either the excitation wavelength or fluorescence wavelength in stages at predetermined intervals and repeatedly varying the other wavelength over a predetermined range at each stage, with a sample contained in a cuvette cell or put in a flow cell. This function provides information about which combination of the fluorescent wavelength and the excitation wavelength gives the highest S/N ratio, thereby enabling a more suitable setting of the wavelengths.

Third Embodiment

Figure 6:
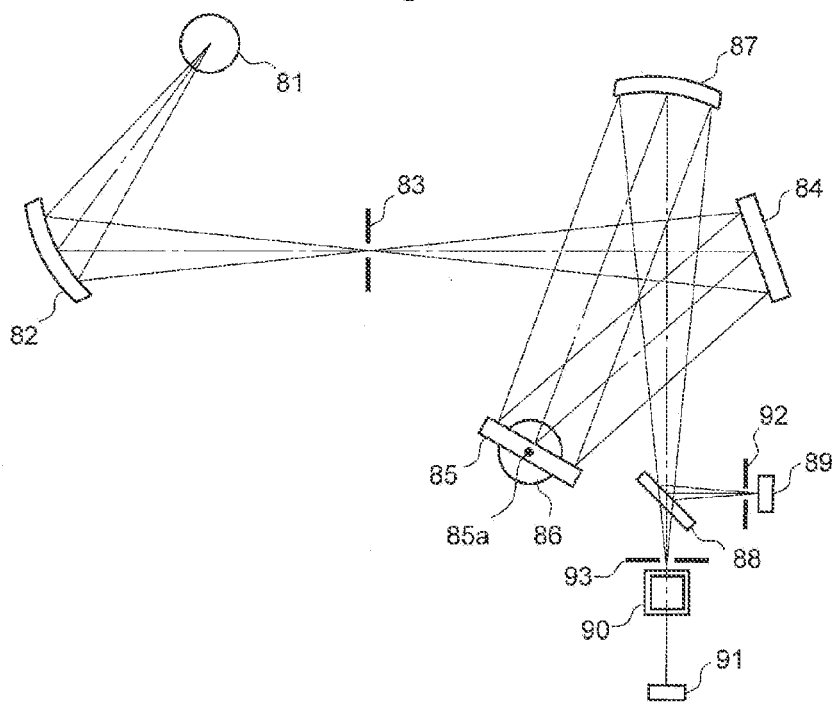
FIG. 6 is a plan view showing the configuration of an optical system of an absorbance determination device according to the third embodiment of the present invention.

One embodiment of the absorbance determination device according to the present invention is hereinafter described. FIG. 6 shows the schematic configuration of an optical system of the absorbance determination device according to the present embodiment. This absorbance determination device is used in an LC system similar to the one shown in FIG. 1 as a detector 50 for sequentially detecting sample components eluted from the column 41.

The light generated by a light source (e.g. deuterium lamp) 81 is collected by a collector mirror 82, passes through an entrance slit 83 and falls onto a mirror 84. The light reflected by the mirror 84 falls onto a diffraction grating 85, to be dispersed in the wavelength direction. The dispersed light falls onto and is reflected by a mirror 87. The reflected light enters a beam splitter 88 and is split into two directions. That is to say, a portion of light passes through the beam splitter 88 and enters a sample cell 90 through a slit 93. The amount of light that has passed through this sample cell 90 (transmission light) is detected by a transmission-light detector 91 composed of a photodiode or the like. The other portion of light is reflected by the beam splitter 88 passes through a slit 92, to be detected by a reference-light detector 89 (e.g. photodiode). The diffraction grating 85 is provided with a grating drive mechanism 86 for rotating the diffraction grating 85 about a rotation shaft 85*a*. The wavelength of light cast into the sample cell 90 (irradiation light) can be arbitrarily set within a predetermined wavelength range by changing the direction of the grating 85 by this grating drive mechanism 86.

Figure 7:
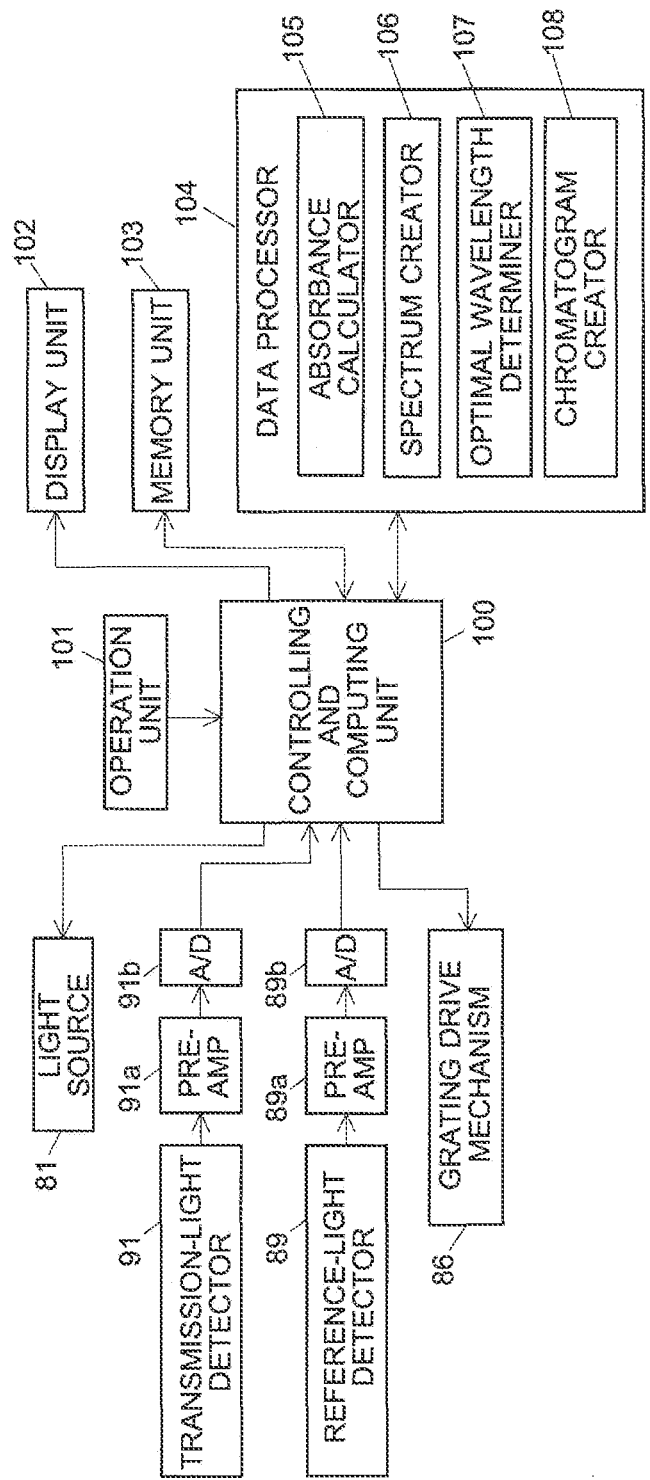
FIG. 7 is a block diagram showing the configuration of a control system of the absorbance determination device according to the same embodiment.

FIG. 7 is a block diagram showing the configuration of a control system of the absorbance determination device according to the present embodiment. The central component of this control system is a controlling and computing unit 100. Users can enter various commands or setting data into this controlling and computing unit 100 through an operation unit 101. A display unit 102 having a monitor is provided to show measurement results or other information. When a user sets the wavelength of the irradiation light and enters a command for energizing the light source and initiating the measurement into the controlling and computing unit 100 through the operation unit 101, the controlling and computing unit 100 energizes the light source 81 and controls the grating drive mechanism 86 so as to rotate the diffraction grating 85 to the position corresponding to the set wavelength. It is also possible to scan a predetermined wavelength range of the irradiation light by controlling the grating drive mechanism 86 so as to rotate the diffraction grating 85 within a predetermined angular range while the light source 81 is on. (This scan operation will be detailed later.) During the measurement, the output currents of the transmission-light detector 91 and the reference-light detector 89 are respectively converted into voltages in preamplifiers 91*a* and 89*a* with a predetermined gain. These voltages are respectively converted into digital data by A/D convertors 91*b* and 89*b*. The controlling and computing unit 100 sequentially sends these digital data to a data processor 104.

The data processor 104 includes an absorbance calculator 105, a spectrum creator 106, an optimal wavelength determiner 107 and a chromatogram creator 108. The absorbance calculator 105 calculates absorbance by dividing the output signal of the transmission-light detector 91 by that of the reference-light detector 89 and computing a negative logarithm of the obtained value (refer to equation (13)). The obtained absorbance data are sequentially sent to the spectrum creator 106 or chromatogram creator 108. Based on this absorbance data, the chromatogram creator 108 creates a chromatogram showing the temporal change of the absorbance. On the other hand, the spectrum creator 106, based on the absorbance data, creates an absorption spectrum showing the absorbance at each wavelength. Furthermore, as will be detailed later, the spectrum creator 106 also creates spectrums showing the output currents of the transmission-light detector 91 and the reference-light detector 89 at each wavelength. These various kinds of spectrums created by the spectrum creator 106 are stored in a memory unit 103. The optimal wavelength determiner 107 performs a predetermined computation based on the spectrums stored in the memory unit 103. (This computation will be detailed later.) It should be noted that the memory unit 103 corresponds to the data memory in the present invention, while the optimal wavelength determiner 107, the absorbance calculator 105 and the spectrum creator 106 in conjunction with each other function as the sensitivity index estimator in the present invention.

The functions of the data processor 104, memory unit 103 and other components may be realized by a dedicated computer inside the main body of the absorbance determination device, or they may be realized by a personal computer having a predetermined program installed therein. In the latter case, the personal computer is connected either directly to the main body of the absorbance determination device, or indirectly to the main body of the device via a system controller connected to each of the devices constituting the aforementioned LC system, and a portion of the functions of the previously described control system is realized by the personal computer.

Figure 8:
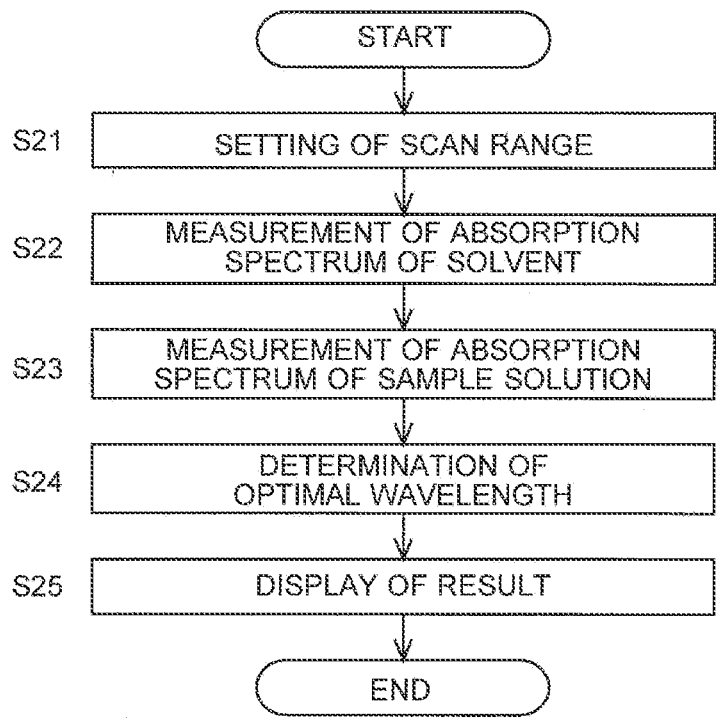
FIG. 8 is a flowchart showing the procedure of determining an optimal wavelength in the absorbance determination device according to the same embodiment.

The procedure of determining the optimal wavelength by the absorbance determination device of the present embodiment is hereinafter described by means of the flowchart of FIG. 8.

(1) Setting of Scan Range (Step S21)

A user performs a predetermined operation on the operation unit 101 to set a range for performing a wavelength scan.

(2) Measurement of Absorption Spectrum of Solvent (Step S22)

Subsequently, with only a solvent (mobile phase) contained in the sample cell 90 (contained in a cuvette cell or put in a flow cell), an absorption spectrum is obtained by varying the wavelength of the irradiation light. Specifically, by using the operation unit 101, the user initially energizes the light source 81 and orders the initiation of the wavelength scan. In response to this operation, the diffraction grating 85 is rotated over an angular range corresponding to the wavelength range set in Step S21. During this process, the signals produced by the fluorescence detector 91 and the reference-light detector 89 are sent to the data processor 104. In the data processor 104, the absorbance calculator 105 sequentially calculates the absorbance of the solvent based on the output signals of the fluorescence detector 91 and the reference-light detector 89. Using the calculated values, the spectrum creator 106 creates an absorption spectrum showing the absorbance of the solvent at each wavelength (this spectrum is hereinafter called the "absorption spectrum of the solvent") and stores it in the memory unit 103.

The spectrum creator 106 calculates the output current of the transmission-light detector 91 backward from the output signal of the A/D convertor 91*b* and the gain of the current-to-voltage conversion by the preamplifier 91*a* to create a spectrum showing the value of the output current of the transmission-light detector 91 at each wavelength, and stores this spectrum in the memory unit 103. (This spectrum is hereinafter called the "current spectrum of the transmission-light detector.") Similarly, the spectrum creator 106 calculates the output current of the reference-light detector 89 backward from the output signal of the A/D convertor 89*b* and the gain of the current-to-voltage conversion by the preamplifier 89*a* to create a spectrum showing the value of the output current of the reference-light detector 89 at each wavelength, and stores this spectrum in the memory unit 103. (This spectrum is hereinafter called the "current spectrum of the reference-light detector.") The set of the absorption spectrum of the solvent, the current spectrum of the transmission-light detector and the current spectrum of the reference-light detector corresponds to the first measurement data in the device according to the third mode of the present invention.

(3) Measurement of Absorption Spectrum of Sample Solution (Step S23)

With the sample cell 90 holding the solvent containing an objective component (this solvent is hereinafter called the "sample solution"), an absorption spectrum showing the absorbance of the sample solution at each wavelength is obtained in the same manner as Step S22 and stored in the memory unit 103. (This spectrum is hereinafter called the "absorption spectrum of the sample solution.") This absorption spectrum of the sample solution corresponds to the second measurement data in the device according to the third mode of the present invention.

(4) Determination of Optimal Wavelength (Step S24)

After the previously described measurements of the spectrum are completed, the controlling and computing unit 100 reads the spectrums obtained in Steps S22 and S23 from the memory unit 103 into the data processor 104, and instructs the optimal wavelength determiner 107 to determine the optimal wavelength. The optimal wavelength determiner 107 subtracts the absorption spectrum of the solvent from that of the sample solution to obtain a spectrum showing the absorbance of the objective component at each wavelength (this spectrum is hereinafter called the "absorption spectrum of the objective component"). Furthermore, the optimal wavelength determiner 107 calculates an estimate of the noise of the absorbance due to the solvent from the current spectrum of the transmission-light detector and that of the reference-light detector.

The noise of the absorbance due to the solvent is estimated as follows: With I denoting the output current of the transmission-light detector 91 and $I_0$ denoting the output current of the reference-light detector 89, the shot noise $\Delta I$ in the transmission-light detector 91 and the shot noise $\Delta I_0$ in the reference-light detector 89 are respectively expressed by $\Delta I = \sqrt{(2qIB)}$ and $\Delta I_0 = \sqrt{(2qI_0B_0)}$, where q is the electron charge, B is the frequency bandwidth in the transmission-light detector, and $B_0$ is the frequency bandwidth in the reference-light detector. Furthermore, with k denoting the gain of the preamplifier 91a in the transmission-light detector 91 and $k_0$ denoting the gain of the preamplifier 89a in the reference-light detector 89, the absorbance $A(I, I_0)$ can be computed by the following equation:

$$A(I, I_0) = -\log\left(\frac{kI}{k_0 I_0}\right) = \log\left(\frac{k_0 I_0}{kI}\right), \quad (13)$$

where log is the common logarithm.

The shot noise $\Delta I$ in the transmission-light detector 91 and the shot noise $\Delta I_0$ in the reference-light detector 89 are the standard deviation of the fluctuation of an electric current. The variance $(\Delta A)^2$ of the noise $\Delta A$ is obtained by the following equation:

$$(\Delta A)^2 = \left(\frac{\partial A}{\partial I}\Delta I\right)^2 + \left(\frac{\partial A}{\partial I_0}\Delta I_0\right)^2 \quad (14)$$

From this equation, the noise $\Delta A$ of the absorbance due to the solvent can be estimated as follows:

$$\Delta A = \sqrt{\left[\frac{\partial A(I, I_0)}{\partial I}\right]^2 [\Delta I]^2 + \left[\frac{\partial A(I, I_0)}{\partial I_0}\right]^2 [\Delta I_0]^2} \quad (15)$$

$$= \sqrt{\left\{\left(\frac{1}{\ln 10} \cdot \frac{1}{I}\right)^2 2qBI + \left(\frac{1}{\ln 10} \cdot \frac{1}{I_0}\right)^2 2qB_0 I_0\right\}}$$

$$= \frac{1}{\ln 10} \sqrt{\frac{2qB}{I} + \frac{2qB_0}{I_0}}$$

where ln represents the natural logarithm.

Since the electron charge q is a constant, the noise $\Delta A$ can be expressed as follows:

$$\Delta A \propto \sqrt{B/I + B_0/I_0} \quad (16)$$

For the purpose of comparing the levels of S/N ratios at different wavelengths, the amount of noise $\Delta A$ computed by the following equation can be used as an alternative:

$$\Delta A = \sqrt{B/I + B_0/I_0} \quad (17)$$

The frequency bandwidth B in the transmission-light detector and the frequency bandwidth $B_0$ in the reference-light detector are normally set to be equal to each other. In this case, the noise $\Delta A$ can be expressed as follows:

$$\Delta A = \sqrt{1/I + 1/I_0} \quad (18)$$

Then, the optimal wavelength determiner 107 calculates an estimate of the S/N ratio at each wavelength by dividing the absorbance value at each wavelength on the absorption spectrum of the objective component by the estimate of the noise of the absorbance due to the solvent determined in the previously described manner, and selects, as the optimal wavelength, the wavelength at which the S/N ratio is maximized.

(5) Display of Result (Step S25)

After the previously described sequential processes have been completed, the controlling and computing unit 100 displays the value of the optimal wavelength determined in Step S24 on the display unit 102. Instead of the value of the optimal wavelength, a graph showing the S/N ratio at each wavelength may be displayed so that the optimal wavelength can be easily and visually located.

A chromatographic analysis by the LC system using the optimal wavelength determined in the previously described manner is performed as follows: By using the operation unit 101, the user initially energizes the light source 81 and sets the optimal wavelength as the wavelength to be used in the measurement. In response to this operation, the diffraction grating 85 is rotated to the angle corresponding to the set optimal wavelength and stopped at that position. Subsequently, when the user orders the initiation of a chromatographic measurement, the measurement of the solvent and the objective component which are sequentially eluted from the column and pass through the flow cell is performed at the optimal wavelength, and a chromatogram with the horizontal axis indicating the retention time and the vertical axis indicating the absorbance is created by the chromatogram creator 108.

As described thus far, with the absorbance determination device according to the present invention, it is possible to determine the wavelength at which the S/N ratio is high and the detection limit is low, so that the measurement can be performed at an optimal wavelength for detecting the objective component. In the previously described procedure, it is possible to determine, instead of the S/N ratio, a value corresponding to the detection limit based on the value obtained by dividing an estimate of the amount of noise due to the solvent by an absorbance value of the objective component at the same wavelength as well as on the concentration of the objective component in the sample solution, and to select, as the optimal wavelength, the wavelength at which the value corresponding to the detection limit is minimized.

In the previous embodiment, when determining the optimal wavelength, the sample to be analyzed (i.e. the solvent or sample solution) is contained in a cuvette cell or put in a flow cell, and the user needs to manually replace the sample and order the initiation of the measurement of the spectrum. However, it is also possible to configure the absorbance determination device according to the present invention so that it automatically performs the measurements of the absorption spectrum at predetermined timings while passing the sample solution through the flow cell. The timing of measuring the spectrum may be determined by a scheduling program stored in the memory unit 103 or the like, or it may be determined by detecting the passage of an objective component based on the output signal produced by the transmission-light detector 91.

In the case of performing an automatic measurement by the scheduling program, the user previously creates, through the operation unit 101, a scheduling program in which the spectrum measurement is scheduled to be performed at a first timing corresponding to a predetermined period of time after the injection of the sample and a second timing corresponding to the elution time of the objective component, and stores that program in the memory unit 103. When the solvent eluted from the column 41 begins to pass through the flow cell 90 and the sample is injected into the solvent channel by the sample injector 30, a trigger signal indicating the timing of the sample injection is generated. Upon receiving this trigger signal directly or via a system controller, the controlling and computing unit 100 begins to control each component of the device according to the scheduling program to obtain an absorption spectrum immediately after the injection of the sample, i.e. at a point in time when only the solvent is present in the flow cell 90, as well as an absorption spectrum at a point in time when both the solvent and the objective component are present in the flow cell 90.

In the case of performing an automatic measurement by detecting the passage of an objective component, after the solvent eluted from the column 41 begins to pass through the flow cell 90, the measurement of the absorption spectrum of the solvent is initially performed immediately after the sample is injected into the solvent channel by the sample injector 30. Subsequently, with the wavelength fixed at a predetermined point, the absorbance signal is monitored, and when the passage of the sample component is detected from a change in the absorbance, the measurement of the absorption spectrum of the solvent containing that component is automatically performed.

In order to more assuredly perform the measurement of the spectrum of the objective component passing through the flow cell 90, it is desirable to temporarily discontinue the flow of the solvent into the flow cell 90 by changing the flow path of the solvent eluted from the column 41 by a channel-switching valve (not shown) or similar device at a timing when the objective component exists in the flow cell 90, and to perform the wavelength scan while the sample component is retained in the flow cell 90.

Figure 9:
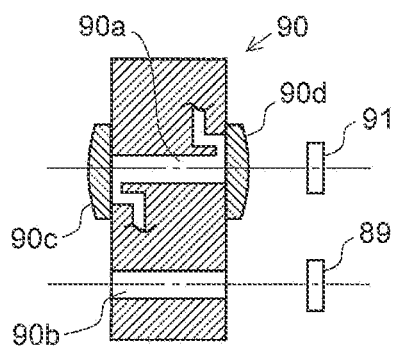
FIG. 9 is a model diagram showing a variation of the sample cell and the detector in the absorbance determination device according to the same embodiment.

In the present embodiment, as shown in FIG. 6, the beam splitter 88 is disposed before the sample cell 90 and the irradiation light is split by the beam splitter 88 into two beams, which are respectively cast into the sample cell 90 and the reference-light detector 89. In place of such a system, a flow cell 90 having a structure as shown in FIG. 9 may be used. The flow cell 90 of FIG. 9 has a channel 90a for allowing the passage of a liquid and a through hole 90b for allowing the passage of light. When an irradiation light collimated by a predetermined device falls onto this flow cell 90, a portion of the irradiation light enters the lens 90c, passes through the channel 90a and falls onto the transmission-light detector 91 in the subsequent stage via the lens 90d. Simultaneously, another portion of the irradiation light passes through the through hole 90b and falls onto the reference-light detector 89 in the subsequent stage. Such a system requires no beam splitter and can be manufactured at a lower cost.

Fourth Embodiment

Figure 10:
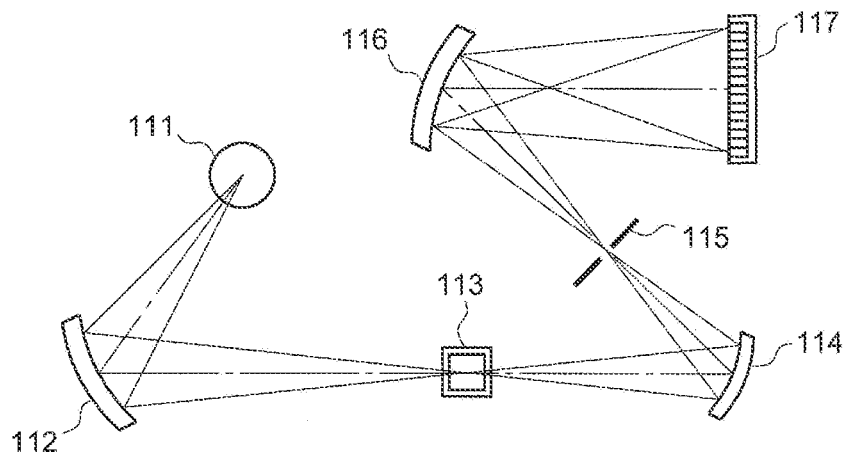
FIG. 10 is a plan view showing the configuration of an optical system of an absorbance determination device according to the fourth embodiment of the present invention.

Another embodiment of the absorbance determination device according to the present invention is hereinafter described. FIG. 10 shows the configuration of an optical system of the absorbance determination device according to the present embodiment. The light generated by a light source (e.g. deuterium lamp) 111 is collected by a collector mirror 112 and cast into a sample cell 113. The light that has passed through the sample cell 113 is collected by a mirror 114 and cast onto a slit 115. The light that has passed through the slit 115 is dispersed by a concave diffraction grating 116 and focused on a multi-channel photodetector 117 composed of a plurality of linearly arranged photodetector elements (e.g. a photodiode array). Since the light dispersed by the diffraction grating 116 in the wavelength direction is simultaneously detected by the multi-channel photodetector 117 at a plurality of wavelengths over a predetermined wavelength range, the present device needs no wavelength scan and requires a shorter period of time to determine the optimal wavelength. The control system, which is not shown, has basically the same configuration as shown in FIG. 7 except for the absence of the grating drive mechanism, the reference-light detector and other components.

Figure 11:
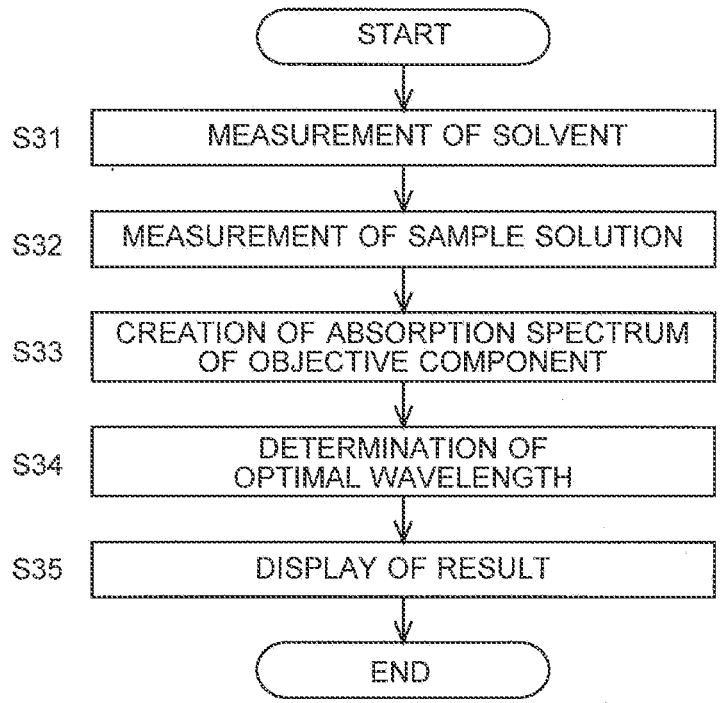
FIG. 11 is a flowchart showing the procedure of determining an optimal wavelength in the absorbance determination device according to the same embodiment.

The procedure of determining the optimal wavelength by the absorbance determination device of the present embodiment is hereinafter described by means of the flowchart of FIG. 11.

Initially, with only a solvent (mobile phase) contained in the sample cell 113, the light from the light source 111 is cast into the sample cell 113, and in this state, the amount of transmission light at each wavelength detected by the multi-channel photodetector 117 is stored in the memory unit 103 (Step S31). Next, with the sample cell 113 holding the solvent containing an objective component (this solvent is hereinafter called the "sample solution"), the amount of transmission light at each wavelength is similarly measured (Step S32).

Based on the ratio between the amount of transmission light of the sample solution measured in this step and that of the solvent stored in the memory unit 103, the absorbance calculator 105 creates a spectrum showing the absorbance of the objective component at each wavelength (this spectrum is hereinafter called the "absorption spectrum of the objective component") by the following equation and stores it in the memory unit 103 (Step S33):

$$A(I_c, I_s) = -\log\left(\frac{kI_c}{kI_s}\right), \tag{19}$$

where k is the gain of the preamplifier for converting an output current of the multi-channel photodetector 117 into a voltage, $I_c$ is the output current of the multi-channel photodetector 117 in the measurement of the sample solution, and $I_s$ is the output current of the multi-channel photodetector 117 in the measurement of the solvent.

Subsequently, the optimal wavelength determiner 107 calculates the output current of each of the photodetector elements of the multi-channel photodetector 117 backward from the output signals of the multi-channel photodetector 117 obtained in the measurement of the solvent (obtained and stored in the memory unit 103 in Step S31), and based on the calculated values, it calculates an estimate of the noise of the absorbance due to the solvent at each wavelength. With $I_s$ denoting the output current of each of the photodetector elements of the multi-channel photodetector 117 in the measurement of the solvent, the shot noise $\Delta I_s$ in each photodetector element is expressed by $\Delta I_s = \sqrt{(2qI_sB)}$, where q is the electron charge and B is the frequency bandwidth. Since the device of the present embodiment has no reference-light detector, the noise of the absorbance is expressed by equation (15) without the terms relating to the reference-light detector. Accordingly, the noise $\Delta A$ due to the solvent can be estimated by the following equation:

$$\Delta A = \frac{1}{\ln 10} \sqrt{\frac{2qB}{I_s}} \quad (20)$$

Given that the frequency bandwidth B and the electron charge q are constants, the amount of noise $\Delta A$ can be expressed as follows if the equation is used to compare the levels of the S/N ratio at different wavelengths:

$$\Delta A = \sqrt{1/I_s} \quad (21)$$

Subsequently, an estimate of the S/N ratio at each wavelength is determined by dividing the absorbance value at each wavelength on the absorption spectrum of the objective component calculated in Step S33 by the estimate of the noise due to the solvent calculated in the previously described manner. Then, the wavelength at which the estimated S/N ratio is maximized is selected as the optimal wavelength (Step S34), and the value of the optimal wavelength is displayed on the display unit 102 (Step S35). The selected optimal wavelength is used, for example, as the wavelength for performing a quantitative analysis of the objective component.

The absorbance determination device according to the present invention is not limited to the previous embodiments; it is allowable to make appropriate changes within the spirit and scope of the present invention. For example, instead of calculating the S/N ratio, it is possible to determine a value corresponding to the detection limit of the concentration by dividing an estimate of the noise due to the solvent by an absorbance value of the objective component at each wavelength and then multiplying it by the concentration of the objective component in the sample solution, and to select, as the optimal wavelength, the wavelength at which the value corresponding to the detection limit is minimized. Furthermore, the absorbance determination device according to the present invention may include a wavelength-setting system for automatically setting the optimal wavelength as the wavelength to be used in the subsequent measurements, in addition to or as an alternative to an informing system for informing a user of the optimal wavelength. In this case, the wavelength at which the estimated S/N ratio is maximized in the calculation by the optimal wavelength determiner 107 is selected as the wavelength to be used in the subsequent measurements and stored in the memory unit 103 by the controlling and computing unit 100. That is to say, in this case, the controlling and computing unit 100 and the memory unit 103 correspond to the wavelength-setting system in the present invention.

In place of the fixed diffraction grating 116 and the multi-channel photodetector 117 as in the present embodiment, it is possible to provide, behind the sample cell 113, a rotatable diffraction grating, a slit through which the diffracted light passes, and a detector for detecting the light that has passed through the slit. In this case, a spectrum data for a predetermined wavelength range can be obtained by rotating the diffraction grating so that the wavelength of the light passing through the slit and falling onto the detector varies over that wavelength range.

If the system shown in FIG. 10 is additionally provided with a reference-light detector, the procedure of determining the optimal wavelength will be the same as described in the third embodiment. In this case, for example, the reference light can be detected by placing a beam splitter between the collector mirror 112 and the sample cell 113 shown in FIG. 10, and collecting, dispersing and detecting the thereby reflected light by means of an additional set of mirror, slit, concave diffraction grating and multi-channel photodetector provided separately from those used for the transmission light.

The absorbance determination device according to the present invention may be provided with the function of creating three-dimensional data composed of the three axes of time, wavelength and absorbance intensity by repeatedly scanning a wavelength range at predetermined intervals of time while passing the solvent and the objective component through the flow cell. In this case, the optimal wavelength at each point in time after the injection of the sample can be determined by performing the previously described calculation using an absorption spectrum obtained immediately after the injection of the sample as the spectrum of the solvent containing no objective component and an absorption spectrum obtained at each subsequent point in time as the spectrum of the solvent containing the objective component. Therefore, by one injection of the sample, it is possible to determine an optimal wavelength for each of the components contained in the sample. Accordingly, each of the sample components temporally separated by and eluted from the column can be detected at an optimal wavelength by making the LC system perform the analysis while temporally varying the wavelength according to a scheduling program in which a previously determined optimal wavelength is set for each point in time after the injection of the sample. Such a scheduling program can be created manually by the user, or automatically by the controlling and computing unit 100, and stored in the memory unit 103.

EXPLANATION OF NUMERALS

51, 81, 111 . . . Light Source
54, 63, 85, 116 . . . Diffraction Grating
60, 90, 113 . . . Sample Cell
59, 89 . . . Reference-Light
66 . . . Fluorescence Detector
91 . . . Transmission-Light Detector
67, 117 . . . Multi-Channel Photodetector
70, 100 . . . Controlling and Computing Unit
71, 101 . . . Operation Unit
72, 102 . . . Display Unit
73, 103 . . . Memory Unit
74, 104 . . . Data Processor
75 . . . Signal Corrector
105 . . . Absorbance Calculator
76, 106 . . . Spectrum Creator
77, 107 . . . Optimal Wavelength Determiner
78, 108 . . . Chromatogram Creator

The invention claimed is:

1. A spectrometric measurement device for casting an irradiation light into or onto a sample and measuring light obtained from the sample due to an interaction between the irradiation light and the sample, comprising:
   a) a data memory for storing first measurement data obtained by using, as the aforementioned sample, a solvent containing no objective component and second measurement data obtained by using, as the aforementioned sample, the solvent containing an objective component, each of the first and second measurement data being obtained by varying, over a redetermined wavelength range, a wavelength of the irradiation light or a wavelength of light to be measured or by dispersing the light obtained from the sample and simultaneously detecting the dispersed light at a plurality of wavelengths within a predetermined range; and b) a sensitivity index estimator for calculating a value indicative of a degree of interaction between the objective component and the irradiation light at each wavelength based on the first measurement data and the second measurement data, for calculating an estimate of an amount of noise due to the solvent at each wavelength from the first measurement data, and for calculating an estimate of a sensitivity index at each wavelength from a ratio between the value indicative of the degree of interaction between the objective component and the irradiation light and the estimate of the amount of noise, wherein:

the aforementioned interaction is an absorption by the sample, and the spectrometric measurement device is an absorbance determination device including an irradiation optical system for casting light into or onto a sample and a transmission-light detector for detecting the light that has passed through the sample;

the data memory is used for storing first measurement data obtained by using, as the aforementioned sample, a solvent containing no objective component and second measurement data obtained by using, as the aforementioned sample, the solvent containing an objective component, each of the first and second measurement data being obtained by varying, over a predetermined wavelength range, a wavelength of the light cast into or onto the sample or a wavelength of the light to be detected, or by dispersing the transmission light from the sample and simultaneously detecting the dispersed transmission light at a plurality of wavelengths within a predetermined range;

the sensitivity index estimator is designed to calculate an absorbance of the objective component at each wavelength based on the first measurement data and the second measurement data, to calculate an estimate of the amount of noise due to the solvent at each wavelength from the first measurement data, and to calculate an estimate of the sensitivity index at each wavelength from a ratio between the absorbance value of the objective component and the estimate of the amount of noise, and the sensitivity index estimator calculates an output current $I_s$ of the transmission-light detector at each wavelength from the first measurement data and calculates an estimate $\Delta A$ of the amount of noise due to the solvent by a following equation:

$$\Delta A = \sqrt{1/I_s} \quad (3)$$

2. A spectrometric measurement device for casting an irradiation light into or onto a sample and measuring light obtained from the sample due to an interaction between the irradiation light and the sample, comprising:

a) a data memory for storing first measurement data obtained by using, as the aforementioned sample, a solvent containing no objective component and second measurement data obtained by using, as the aforementioned sample, the solvent containing an objective component, each of the first and second measurement data being obtained by varying, over a redetermined wavelength range a wavelength of the irradiation light or a wavelength of light to be measured or by dispersing the light obtained from the sample and simultaneously detecting the dispersed light at a plurality of wavelengths within a predetermined range; and b) a sensitivity index estimator for calculating a value indicative of a degree of interaction between the objective component and the irradiation light at each wavelength based on the first measurement data and the second measurement data, for calculating an estimate of an amount of noise due to the solvent at each wavelength from the first measurement data, and for calculating an estimate of a sensitivity index at each wavelength from a ratio between the value indicative of the degree of interaction between the objective component and the irradiation light and the estimate of the amount of noise, wherein:

the aforementioned interaction is an absorption by the sample, and the spectrometric measurement device is an absorbance determination device including an irradiation optical system for casting light into or onto a sample and a transmission-light detector for detecting the light that has passed through the sample;

the data memory is used for storing first measurement data obtained by using, as the aforementioned sample, a solvent containing no objective component and second measurement data obtained by using, as the aforementioned sample, the solvent containing an objective component, each of the first and second measurement data being obtained by varying, over a predetermined wavelength range, a wavelength of the light cast into or onto the sample or a wavelength of the light to be detected, or by dispersing the transmission light from the sample and simultaneously detecting the dispersed transmission light at a plurality of wavelengths within a predetermined range;

the sensitivity index estimator is designed to calculate an absorbance of the objective component at each wavelength based on the first measurement data and the second measurement data, to calculate an estimate of the amount of noise due to the solvent at each wavelength from the first measurement data, and to calculate an estimate of the sensitivity index at each wavelength from a ratio between the absorbance value of the objective component and the estimate of the amount of noise;

a reference-light detector for detecting the light cast into or onto the sample is provided; and the sensitivity index estimator calculates the absorbance of the objective component at each wavelength by subtracting an absorption spectrum obtained from the first measurement data from an absorption spectrum obtained from the second measurement data, calculates an output current I of the transmission-light detector and an output current $I_0$ of the reference-light detector at each wavelength from the first measurement data, and calculates an estimate $\Delta A$ of the amount of noise due to the solvent at each wavelength by a following equation:

$$\Delta A = \sqrt{B/I + B_0/I_0} \quad (4)$$

where B is a frequency bandwidth used in the transmission-light detector and its signal processing, and $B_0$ is a frequency bandwidth used in the reference-light detector and its signal processing.

3. The spectrometric measurement device according to claim 1, comprising a wavelength-setting system for setting, as a wavelength to be used in a subsequent measurement, a wavelength at which the estimate of the sensitivity index calculated by the sensitivity index estimator equals a value corresponding to a highest sensitivity level.

4. A non-transitory computer readable medium storing a program for making a computer function as the data memory and the sensitivity index estimator described in claim 1.

5. The spectrometric measurement device according to claim 2, comprising a wavelength-setting system for setting, as a wavelength to be used in a subsequent measurement, a wavelength at which the estimate of the sensitivity index calculated by the sensitivity index estimator equals a value corresponding to a highest sensitivity level.

6. A non-transitory computer readable medium storing a program for making a computer function as the data memory and the sensitivity index estimator described in claim 2.

\* \* \* \* \*